United States Patent [19]

Dill

[11] 4,273,540
[45] Jun. 16, 1981

[54] THERAPIST'S PATIENT EVALUATION AND TRAINING DEVICE

[76] Inventor: Randy B. Dill, 49 Walnut St., Ambler, Pa. 19002

[21] Appl. No.: 141,216

[22] Filed: Apr. 17, 1980

[51] Int. Cl.³ .............................................. G09B 23/28
[52] U.S. Cl. ..................................... 434/262; 434/236
[58] Field of Search ............... 35/5, 6, 17, 22 R, 29 R

[56] References Cited

U.S. PATENT DOCUMENTS

| | | | |
|---|---|---|---|
| 1,487,115 | 3/1924 | McQuarrie | 35/5 UX |
| 2,053,874 | 9/1936 | O'Donnell | 35/5 |
| 2,931,108 | 4/1960 | Brown | 35/5 |
| 3,657,456 | 4/1972 | Kozak | 35/29 R X |
| 3,751,825 | 8/1973 | Barrett | 35/6 |

Primary Examiner—Harland S. Skogquist
Attorney, Agent, or Firm—Howard E. Sandler

[57] ABSTRACT

A therapist's patient evaluation and training device and more particularly such a device for evaluating disorders of brain damaged patients and of patients who have suffered trauma to or disease of the central nervous system and for aiding such patients in obtaining confidence to overcome such deficiencies to the utmost of their respective residuary capacities.

10 Claims, 3 Drawing Figures

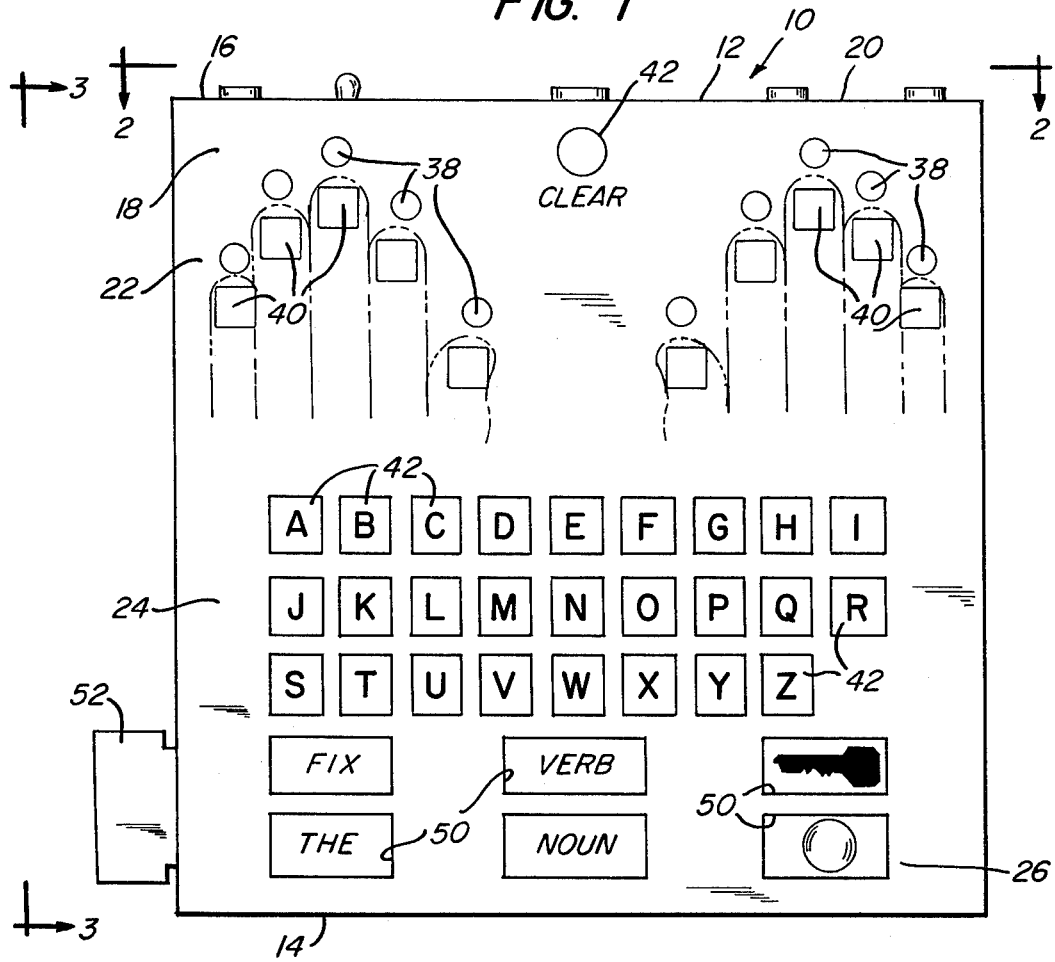
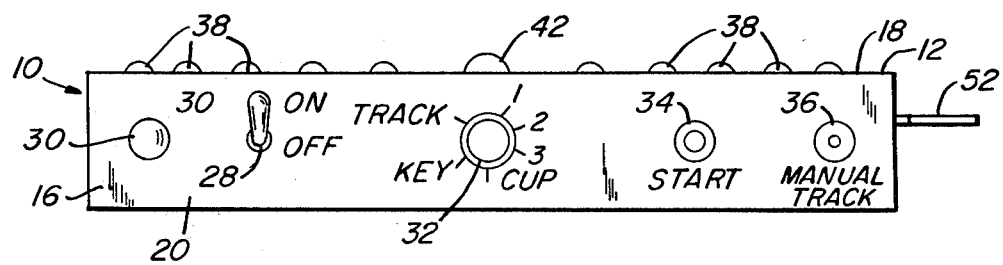
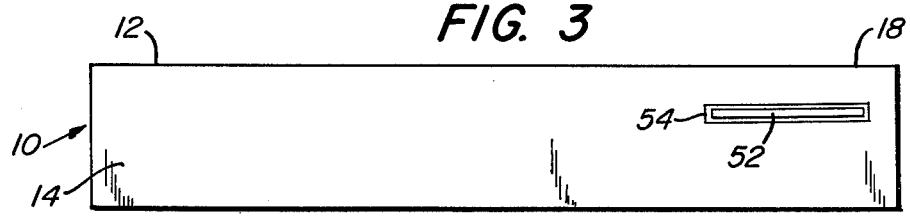

THERAPIST'S PATIENT EVALUATION AND TRAINING DEVICE

Many patients who have or are suffering from brain lesions, brain disorders, disturbances of the cerebral cortex, strokes, trauma to or disease of the central nervous system, and the like, have resultant symptomatic disorders which manifest themselves in a variety of fashions, for example: a total or partial loss of the power to use or understand words; an impairment or loss of the power to perform purposeful movements; an impairment in the ability to recognize objects or their uses; and the like. In pathology, many of these resultant disorders are commonly referred to as aphasia, apraxia and agnosia.

Medical assistance to aphasia, apraxia and agnosia patients in the forms of surgery and drug related treatments are successful to only a limited extent. Absent such drug and surgical assistance, and in some cases in lieu of, the patient's best hope for subsequent recovery or alleviation of the aphasia, apraxia and agnosia disorders or handicaps often reside in re-education and therapy which are based on the patient's mental and physical condition and the unknown force provided in humans and animals by nature for overcoming or compensating for handicaps.

On occasion, totally astounding and unexpected partial and complete instantaneous recoveries for aphasia, apraxia and agnosia patients occur which are only explainable by an unknown quirk of nature; however, for the most part, such instantaneous recoveries are rare indeed. In fact, most partial or complete recoveries or compensations for these conditions are the result of difficult and time consuming work on the part of speech, occupational and physical therapists and their patients. Furthermore, a working rapport must be established between the therapist and his patient and the patient's attitude must be such that he is willing and, indeed eager, to participate in the therapy. The establishment of a working rapport as well as a positive patient attitude are among the key subjective tools which a therapist attempts to finally tune to complete a successful treatment plan.

A therapist working with aphasia, apraxia and agnosia patients must initially establish preliminary data which defines the extent of brain damage and must thereafter continually monitor and up-date this data for progress evaluations and determinations of subsequent therapy treatment and goals. The establishment of the initial data presents the first hurdle that the therapist must overcome. Specifically, the therapist must establish an instant working rapport with the patient to gain the patient's confidence and cooperation. Accordingly, the initial meeting with the patient is of extreme importance. On many occasions, the onslaught of the brain damage to the patient has been sudden. The very suddenness of this damage is frightening to the patient. Furthermore, the patient may still be able to think rationally and clearly with respect to many matters; however, he may find that he cannot spell or read or understand verbal directions. This inability to perform simple tasks while still possessing his intellect often will confuse the patient. This frightened and confused attitude may result in the patient becoming depressed and withdrawing and/or becoming angry at anyone connected with the medical field for they have not been able to "cure" him.

The above attitude problems often confront the therapist when he initially meets the patient. Furthermore, the patient's attitude may be worsened by prior contacts with nurses, medical doctors and technicians. These prior contacts were more concerned with the patient's immediate medical well-being and because of his physical problems by necessity may have been brusque or caused him physical pain or other discomforts.

In many instances, such attitude problems have caused therapists to lose the patient's confidence at the initial meeting. When a therapist first meets the patient and immediately begins to question him to determine the extent of the damage the patient may withdraw or turn hostile. After all, the patient has been questioned by countless doctors, residents and interns. Nurses may have brought him out of a drug-induced sleep by yelling in his ear and requesting him to tell them his name, or to move his right finger or to tell them what year it is. The patient is simply tired of question and answer sessions. On the other hand, the therapist may use "flash cards" as a tool to determine whether the patient can identify visually or verbally. The use of the flash cards can be taken by an adult or even younger patients to be demeaning and identifiable with very young children. The patient does not wish to be treated as a child, and hence, not as a full participant. The therapist might even attempt to use complex machinery for his evaluation; however, given the circumstances of the patient's prior attitude; oscilloscopes, electrical stimulations and machinery hum (coupled with the common stark and bright locations of this machinery), such a usage may be detrimental to the establishment of the proper rapport between the therapist and his patient. Once the initial rapport between the patient and therapist is established, the maintenance thereof must be continued throughout the often long and arduous therapy program. Accordingly, it is best for insuring this continued relationship that the therapist's treatment and/or analytical pattern does not fall back to a clinical or business-type approach.

By means of the present invention which includes a compact and attractive monitor which is selectively operable in a plurality of modes to establish an interaction between the therapist and the patient, the hereinabove-mentioned problems which may occur are overcome or, in the least, greatly alleviated. Specifically, the monitor of the present invention is selectively operable in an unobtrusive and indeed a pleasant manner to enable the therapist to determine the patient's ability to follow directions, spelling ability, recognition response, digit dexterity, visual field damage, and to aid in the re-education of the patient. The utilization of the monitor aids in establishing a relaxed anxiety-free atmosphere and thus improves the patient's response and willingness to participate.

These and other objects and advantages of the present invention will become more readily apparent upon a reading of the following description and drawings in which:

FIG. 1 is a plan view of one preferred embodiment of a therapist's patient evaluation and training device or monitor constructed in accordance with the principles of the present invention;

FIG. 2 is a side view taken on lines 2—2 of FIG. 1 and more particularly illustrating the monitor controls which are selectively operable by the therapist; and FIG. 3 is an end elevational view taken on lines 3—3 of FIG. 1.

Referring to the drawings there is illustrated therein a therapist's patient evaluation and training device or monitor of the present invention which is generally indicated at 10. Monitor 10 is of the type for utilization by a therapist in working with brain damaged patients; for example, those suffering from aphasia, apraxia and agnosia and comprises a compact attractive generally rectangular closed casing 12, forward and rear walls 14 and 16, respectively, and a generally planar upper surface 18. In use, the forward wall 14 faces the patient and the rear wall 16 faces the therapist. As is best illustrated in FIG. 2, a selectively operable therapist's operating and adjusting means 20 is incorporated within rear wall 14. At this location, the operating and adjusting means 20 is hidden from the patient's view thereby negating any tendency for the patient to be confused by the appearance of the means 20 as well as maintaining a visual barrier such that the patient cannot observe the selective operation of the means 20 by the therapist.

It is to be noted that for purposes of description hereinbefore and hereinafter, forward and rearward and front and rear shall refer respectively to towards and away from the forward wall 14 as viewed in FIG. 1. Furthermore, upper and lower or upwardly and downwardly shall similarly be as monitor 10 is viewed in FIG. 1.

The operating and adjusting means 20 is selectively adjustable by the therapist to control the energization and operation of at least portions of the diagnostic and education sections which are incorporated within the upper surface 18. As is illustrated, such diagnostic and education sections include: an electrical responsive digit section 22; an electrical responsive alphabetic section 24; and a manual graphic insert section 26.

Operating and adjusting means 20 comprises: a suitable "on-off" energization selector switch 28; a power indicator light 30 which is in suitable electrical communication with selector switch 28 to light up when selector switch 28 is in the "on" position to thus indicate that monitor 10 is energized; a mode selector switch 32 which is selectively operable by the therapist to cause the digit section 22 and alphabetic section 24 to be operable in a plurality of pre-determined modes or sequences; a start push button 34 which, when depressed, initiates the sequence selected by mode selector switch 32; and an alpha track push button 36 which is manually operable by the therapist in a manner to be described hereinafter.

Digit section 22 comprises a plurality of electrically coupled sets of aligned lights 38 and pressure sensitive digit switch means 40. The respective sets of lights 38 and switch means 40 are arranged in left and right hand arrays to approximate spacing between the digits of the left and right hands. As will be discussed hereinafter, the digit section 22 is operable in response to the positioning of mode selector switch 32 to any of the numeral "1", "2" or "3" positions. The upper surfaces of switch means 40 are opaque and each switch means 40 includes a suitable illumination arrangement therebehind such that when pressure is applied to respective switch means 40, the respective upper surface thereof is illuminated.

Alphabetic section 24 comprises a plurality of pressure sensitive switch means 42. As illustrated, there are twenty-six switch means 42 arranged in three horizontal rows each of which has a respective letter of the English language alphabet thereon, arranged in sequential order. The upper surfaces of switch means 42 are opaque and each switch means 42 includes a suitable illumination arrangement therebehind such that when pressure is applied to respective switch means 42, the respective upper surface thereof is illuminated. As will also be discussed hereinafter, the alphabetic section 24 is operable in response to the positioning of mode selector switch 32 to the cup, key and track positions.

A clear push button 44 is positioned in a rearward portion of the upper surface 18. Clear push button 44 is suitably electrically connected to the circuitry for switch means 40 and 42 and lights 38 such that upon depression thereof, all illuminated lights are extinguished.

At this point, it is to be noted that the invention herein is primarily to a monitor 10 which is operable in an unobtrusive manner to establish an interaction between the therapist and the patient and to aid the therapist in determining the patient's ability to follow directions, spelling ability, recognition response, digital dexterity, visual field damage and to aid in the re-education of the patient. Furthermore, the design of the logic and circuitry to achieve the purposes of the present invention may be accomplished easily by one skilled in the art of electronics in a variety of known fashions. As such, the specific design of the logic and circuitry does not form a portion of the instant invention nor is a schematic thereof necessary for a full and complete understanding of the invention herein. Similarly, the structural configuration of items such as switch means 40 and 42 may be of any suitable construction (i.e., spring biased, pressure sensitive, field type, and the like) and detailed illustrations thereof are not necessary for a full and complete understanding of the invention herein. For various types of switch means which are operable to complete discreet circuits reference is hereby made to U.S. Pat. Nos.: 2,855,703 (see spring biased switch assembly at FIG. 4); 2,154,478 (see spring biased arrangement at FIG. 7); 2,931,108 (see keyboard arrangement and circuitry therefor at FIGS. 1 thru 3); 3,751,825 (see electromechanical step switch circuit at FIG. 4); and the like.

The digit section 22 is made operable by rotating the mode selector switch 32 to the mode "1", "2" or "3" positions and thereafter depressing the start button 34 to initiate the preprogrammed sequencing. The logic for such pre-programmed sequencing can be accomplished in any suitable manner (i.e. solid state electronics) which will control the required electrical energization and de-energization of the display components in the desired manner.

In mode "1", the sequence will initiate by the light 38 adjacent the right thumb position becoming illuminated. The patient is then directed to depress the adjacent switch means 40 with his right thumb. Upon depression of the switch means 40 a suitable indicating light below an opaque surface of the right thumb switch means 40 will illuminate. Thus, both the patient and the therapist see visual proof of the patient's success in dexterity, visual field and following verbal directions. If the patient's condition is such that he cannot follow verbal directions, the therapist can illustrate to the patient by way of visual example specifically the manner in which the patient is to participate. Thus, even absent an ability to understand verbal directions, the patient may be able to participate in the sequencing of the digit section 22 in mode "1". After the illumination of the light 38 and switch means 40 adjacent the right thumb, the therapist depresses the clear button 44 which will cause such light 38 and switch means 40 to extinguish and then the light 38 adjacent the next digit in the right hand will illuminate. The patient then depresses the switch means 40 adjacent this newly illuminated light 38. Such a sequence will continue in mode "1" for all digits of the right hand and thereafter the sequence will shift to the left hand initiating with the light 38 adjacent the left thumb.

Rotating the selector switch to mode "2" results in a similar action as in mode "1" except rather than the illumination of lights 38 being in a predetermined sequential pattern, such illumination will be random. Thus, in mode "2" the therapist will be able to determine that the patient's ability to perform properly is in fact genuine recognition and is not a function of anticipating the sequential pattern. Furthermore, the ability to rapidly complete a series of random tasks is measurably more difficult than completing a series of sequential tasks. Thus, in using the monitor 10 of the present invention, the therapist can work to the patient's own individual level and need not frustrate the patient by switching to an advanced mode (i.e., mode "2") until the patient is confident in his ability to complete the sequencing of mode "1".

Mode "3" is quite similar to mode "2"; however, in mode "3", two or three lights 38 will become illuminated simultaneously and the patient must depress the switch means 40 adjacent each of these lights 38. The logic incorporated in mode "3" may be such that all adjacent switch means 40 must be depressed simultaneously in order for them to become illuminated.

The alphabetic section 24 is made operable by rotating the mode selector switch 32 to the cup, key or track modes. In the cup mode, the logic will permit only the letters C-U-P of the alphabetic section to become illuminated. If desired, such logic may also include that the letters C-U-P must be depressed sequentially in order for illumination to occur. The patient may orally be told to spell "cup" or a figure of a cup may be displayed in the insert section 26 with instructions to the patient to identify and spell such figure. The key mode is similar to the cup mode and provides further information to the therapist insofar as the patient's abilities.

The track mode is designed to monitor visual field damage which may exist with patients who have suffered trauma to or disease of the central nervous system, aphasia, apraxia and agnosia disorders, and the like. The track mode will aid the therapist in determining if visual field damage does in fact exist and to monitor the resultant "blind spot" area. In the track mode, the switch means 42 will become illuminated in a predetermined sequence by the therapist successively depressing the track button 36. For example, the track mode may be programmed to first light up the switch means 42 bearing the letter "A". The patient is requested to identify the illuminated letter. After proper identification, or failure to identify by the patient, the therapist will depress the track button 36 which will cause the existing illuminated switch means 42 to extinguish and the next switch means 42 in the predetermined sequence to illuminate and so on until the entire sequence of all of the switch means 42 is completed.

The manual graphic insert section 26 is simply a plurality, as shown six, openings or transparent windows 50, which are formed in the upper surface 18. A slot 54 within a side wall and a suitable card supporting arrangement is provided within casing 12 to permit the selective insertion and supporting of card 52. Various words, pictorial illustrations or the like are arranged on card 52 in a manner that when card 52 is received within slot 54, the respective words and pictorial illustrations will register within the respective windows 50 therefor. The operator may then utilize these words or illustrations as part of his evaluation technique either independently or in conjunction with the alphabetic section 24. To aid in the combined usage of insert section 26 in conjunction with the alphabetic section 24 it is envisioned that selector switch 32 would have still another position which would permit any switch means 42 to be illuminated upon the depression thereof. In such an instance, the depression of clear key 44 would extinguish the illumination of all illuminated switch means 42.

The electrical energization for the monitor 10 may be from any suitable source; for example, a standard 110 A.C. supply or by battery operation. Such a selection of electrical energization source, just as the particular logic, switching and display components, is simply a matter of design choice and is not a part of the invention herein.

The invention herein is primarily to a therapist's patient evaluation and training device for evaluating disorders of brain damaged patients in an unobtrusive, non-clinical manner and for aiding such patients in obtaining confidence to overcome such deficiencies. Accordingly, various modifications may be made by those skilled in the art to the particular embodiment of the invention described herein without departing from the scope of the invention which is defined by the claims set forth hereinafter. For example: suitable timing circuits and recording means may be incorporated within the monitor 10; the therapist's operation and adjusting means may be a separate unit umbilically connected to the casing 12; a scrambling of the sequence of letters in the alphabetic section 24; other types of plug-in type logic circuits may be designed which are selectively interchangeable within the monitor 10; and the like.

What is claimed is:

1. A therapist's patient evaluation and training device for use in evaluating disorders of brain damaged patients and of patients who have suffered damage to the central nervous system, comprising: a casing having an upper surface; a digit section carried by said casing and including a plurality of spaced electrically energizable digit means arranged in an array approximating the five digits of at least one hand; a keyboard section carried by said casing and including a plurality of spaced electrically energizable keyboard means having indicia thereon; each of said digit and keyboard means including portions thereof operable to produce respective discreet illuminations adjacent said upper surface upon appropriate actuation thereof by a patient; control means selectively operable by a therapist to render said digit and keyboard sections operable in a plurality of modes; during one of said modes said digit means are cycled through a first digit means operational sequence and during other of said modes said digit means are cycled through a second digit means operational sequence; and during another of said modes said keyboard means are cycled through a first keyboard means operational sequence and during still another of said modes said keyboard means are cycled through a second keyboard means operational sequence.

2. A therapist's patient evaluation and training device as is specified in claim 1 wherein one of said first and second digit means operational sequences is predetermined and other of said first and second digit means operational sequences is random.

3. A therapist's patient evaluation and training device as is specified in claim 2 wherein said digit section includes a visual indicating means adjacent each of said digit means, said visual indicating means being operable in response to said control means to illuminate in an appropriate operational sequence as a signal to the patient to actuate the digit means adjacent to the illuminated visual indicating means.

4. A therapist's patient evaluation and training device as is specified in claim 3 wherein said plurality of digit means are arranged in two arrays, each of which approximate the five digits of a respective hand.

5. A therapist's patient evaluation and training device as is specified in claim 2 wherein said indecia are letters of an alphabet.

6. A therapist's patient evaluation and training device as is specified in claim 5 wherein during at least one of said first and second keyboard means operational sequences, the respective operational sequence therefor is to spell a predetermined word and only the keyboard means containing the respective letters of the alphabet for such a word will illuminate upon the actuation thereof by a patient.

7. A therapist's patient evaluation and training device as is specified in claim 1 wherein one side of said casing faces the patient, the side thereof opposite said one side faces the therapist and the selective operation of said control means is by manipulation of control portions thereof, which said control portions are carried by said casing adjacent said opposite side and at an elevation below said upper surface.

8. A therapist's patient evaluation and training device as is specified in claim 1 wherein when said keyboard section is operable said digit section is inoperable and when said digit section is operable said keyboard section is inoperable.

9. A therapist's patient evaluation and training device as is specified in claim 1 additionally including a manually interchangeable display section carried by said casing adjacent said upper surface.

10. A therapist's patient evaluation and training device as is specified in claim 1 additionally including selectively operable extinguishing means carried by said casing and operable upon actuation thereof to extinguish all illuminations of said digit and keyboard means.

* * * * *